United States Patent [19]

Vander Meer et al.

[11] Patent Number: 4,921,696

[45] Date of Patent: May 1, 1990

[54] METHOD FOR THE CONTROL OF INSECTS

[75] Inventors: Robert K. Vander Meer; Clifford S. Lofgren; David F. Williams, all of Gainsville, Fla.

[73] Assignees: The United States of America as represented by the Secretary of Agriculture, Washington, D.C.; Southern Research Institute, Inc., Birmingham, Ala.

[21] Appl. No.: 256,237

[22] Filed: Oct. 11, 1988

Related U.S. Application Data

[63] Continuation of Ser. No. 758,856, Jul. 26, 1985, abandoned, which is a continuation of Ser. No. 455,727, Jan. 5, 1983, abandoned, which is a continuation-in-part of Ser. No. 598,908, Apr. 16, 1984, abandoned, which is a continuation of Ser. No. 361,501, Mar. 25, 1982, abandoned.

[51] Int. Cl.$^5$ .................. A01N 25/00; A01N 37/06; A01N 41/06; A01N 55/02

[52] U.S. Cl. ...................... 424/84; 514/494; 514/502; 514/538; 514/547; 514/549; 514/550; 514/553; 514/562; 514/601; 514/605

[58] Field of Search ............... 514/601, 605, 494, 502, 514/538, 547, 549, 550, 553, 562; 424/84

[56] References Cited

U.S. PATENT DOCUMENTS

| | | | |
|---|---|---|---|
| 2,003,615 | 6/1935 | Smith et al. | 103/136 |
| 2,346,612 | 4/1944 | Rothrock | 260/78 |
| 2,732,378 | 1/1956 | Cavillito | 260/296 |
| 2,759,019 | 8/1956 | Brown et al. | 260/556 |
| 2,803,656 | 8/1957 | Ahlbrecht et al. | 260/556 |
| 2,915,554 | 12/1959 | Ahlbrecht et al. | 260/556 |
| 3,220,921 | 11/1965 | Greenbaum et al. | 424/352 |
| 3,398,182 | 8/1968 | Guenthner et al. | 260/455 |
| 3,734,962 | 5/1973 | Niederdrum et al. | 260/556 F |
| 3,787,351 | 1/1974 | Olson | 260/40 R |
| 3,795,743 | 3/1974 | Okuda et al. | 424/321 |
| 3,925,555 | 12/1975 | Okuda et al. | 424/321 |
| 3,991,209 | 11/1976 | Forsyth et al. | 424/321 |
| 4,101,468 | 7/1978 | Perrey et al. | 521/115 |
| 4,152,436 | 5/1979 | Drabb | 424/251 |
| 4,176,176 | 11/1979 | Cella et al. | 424/321 |
| 4,424,178 | 1/1984 | Daubenbuchel et al. | 264/40.1 |
| 4,518,594 | 5/1985 | Kasamatsu et al. | 514/155 |
| 4,767,446 | 8/1988 | Konishi et al. | 71/103 |

FOREIGN PATENT DOCUMENTS

| | | | |
|---|---|---|---|
| 48-32650 | 10/1973 | Japan | 424/321 |
| 48-34208 | 10/1973 | Japan | 424/321 |
| 57-156407 | 9/1982 | Japan | |
| 738758 | 10/1955 | United Kingdom | |
| 873590 | 7/1961 | United Kingdom | |

OTHER PUBLICATIONS

Banks, W. A. et al., "Laboratory and Field Evaluation of Several Organochlorine and Organophosphorus Compounds for Control of Imported Fire Ants" ARS-S-169 ARS-USDA Oct. 1977.

Harlan, D. P. et al., "Large Area Tests of AC-217,300 Bait for Control of Imported Fire Ants in Alabama, Louisiana, and Texas" Southwest Entomologist, vol. 6, pp. 150–157, 1981.

Burden, G. S., "Comparison of Insecticide Baits Against Five Species of Cockroaches" Pest Control, vol. 48, pp. 22–24, 1980.

*Primary Examiner*—Allen J. Robinson
*Attorney, Agent, or Firm*—Jones, Askew & Lunsford

[57] ABSTRACT

A method has been discovered for the control of arthropod pests which comprises treating the pest with an effective amount of selected fluorocarbons.

49 Claims, No Drawings

METHOD FOR THE CONTROL OF INSECTS

This application is a continuation of Ser. No. 758,856 filed July 26, 1985, which was a continuation of Ser. No. 455,727 filed Jan. 5, 1983, and a continuation-in-part of Ser. No. 598,908 filed Apr. 10, 1984, which was a continuation of Ser. No. 361,501 filed Mar. 25, 1982, all now abandoned.

PRIOR ART

Discovering pesticides that are effective against a broad range of insect pests and that also can be used safely on crop lands and pastures has long been a problem. One such problem area has been in the control of ants and related insects. Particularly destructive are fire ants (such as *Solenopsis invicta*) which sting humans and livestock, feed on crop seedlings and germinating seeds thereby reducing yields, and damaging equipment which strike their mounds. Requirements for an effective pesticide formulation for the control of fire ants has been characterized as being (1) not repellent to the ants, (2) readily transferrable from one ant to another, and (3) exhibiting delayed toxicity. Repellency can reduce or negate the effectiveness of a toxicant because the ants will avoid the treated bait. The treated bait must be transferable either by carrying it back to the nest or by trophallaxis, and the toxicity must be delayed because foraging ants constitute only a small percentage of the total colony and must survive long enough to pass the toxicant onto the main colony population, especially the queen. It is preferable that the formulations exhibit delayed toxicity over a wide range of pesticide concentration because the active ingredient becomes diluted during trophallaxis (Banks et al, ARS-S-169, October 1977). Presently only one commercially available pesticide (Amdro U.S. Pat. No. 4,152,436) is registered as a bait for outdoor control of fire ants such as *Solenopsis invicta, S. xyloni, S. richteri,* and other ants including *Pheidole megacephala* and *Iridomyrmex humilis.* Amdro is also effective against Lepidopterous larvae. However, it cannot be applied to edible crops. The insecticide Mirex (U.S. Pat. No. 3,220,921) is also known to be effective against fire ants, but is no longer registered for use.

SUMMARY OF THE INVENTION

We have discovered a method and a composition for the control of a population of arthropods including ants, cockroaches, flies, mosquitoes, and termites. The method comprises treating the pests with an effective amount of a toxicant substance or mixture of substances of the formula $$R_fSO_2A$$

wherein $R_f$ is a fluoroaliphatic radical containing up to 20 carbon atoms and A is a structurally compatible residue, or agriculturally acceptable salts of the toxicant substance or substances. The compositions in accordance with the invention comprise the above toxicant substance or mixture of substances and a bait component.

The fluoroaliphatic radical, $R_f$, is a fluorinated, monovalent moiety which is straight chain, branched chain, and if sufficiently large, cyclic, or combinations thereof, such as alkylcycloaliphatic radicals. The skeletal chain can include catenary oxygen and/or trivalent nitrogen hetero atoms bonded only to carbon atoms, such hetero atoms providing stable linkages between fluorocarbon groups and not interferring with the chemically inert character of the $R_f$ radical. While $R_f$ can have a large number of carbon atoms, compounds where $R_f$ is not more than 20 carbon atoms will be adequate and preferred since large radicals usually represent a less efficient utilization of fluorine than is possible with smaller $R_f$ radicals. Generally, $R_f$ will have up to 20 carbon atoms, preferably 5 to about 12. The terminal porton of the $R_f$ group has preferably at least three fully fluorinated carbon atoms, e.g., $CF_3CF_2CF_2—$, and the preferred compounds are those in which the $R_f$ group is fully or substantially completely fluorinated, as in the case where $R_f$ is perfluoroalkyl, $C_nF_{2n+1}$.

In the above formula A is a structurally compatible residue (i.e., capable of being linked to the $SO_2$ radical) which includes the radicals $NR_1R_2$ and $OR_4$ wherein $R_1$ and $R_2$ are selected from the group consisting of H, alkyl, alkenyl, alkynyl, aryl, aralkyl, aroyl, acyl, cycloalkyl, cycloalkenyl, cycloalkynyl, a heterocyclic ring containing atoms selected from the group consisting of C, N, S or O, hydroxyalkyl, haloalkyl, aminoalkyl, carboxyalkyl salts, esters and amides, or a group of the structure $—(C_xH_{2x}O)_n(C_yH_{2y}O)mR_3$ wherein $n+m=1-20$, x and y are 1-4 and $R_3$ is selected from the same group as $R_1$ and $R_2$; and wherein $R_4$ is H, aryl, a heterocyclic ring or an alkaline earth, alkali metal, organic amine or ammonium cation. The formula $NR_1R_2$ also includes radicals in which N, $R_1$ and $R_2$ are taken together to form a ring the atoms of which are selected from the group consisting of C, N, S or O.

The salts of the invention are generally metal, ammonium or organic amine and quaternary amine salts and can be prepared by treating the acid-form compund with an appropriate base under mild conditions. Among the metal salts of the invention are alkali metal (e.g., lithium, sodium and potassium), alkaline earth metal (e.g., barium, calcium and magnesium) and heavy metal (e.g., zinc and iron) salts as well as other metal salts such as aluminum. Appropriate bases for use in preparing the metal salts include metal oxides, hydroxides, carbonates, bicarbonates and alkoxides. Some salts are also prepared by cation exchange reaction (by reacting a salt of the invention with an organic or inorganic salt in a cation exchange reaction). The organic amine salts include the salts of aliphatic (e.g., alkyl), aromatic and heterocyclic amines, as well as those having a mixture of these types of structures. The amines useful in preparing the salts of the invention can be primary, secondary or tertiary and preferably contain not more than 20 carbon atoms. Such amines include, for example, morpholine, methyl cyclohexylamine, glucosamine, amines derived from fatty acids, etc. The amine and ammonium salts can be prepared by reacting the acid form with the appropriate organic base or ammonium hydroxide. Any of the salts of the types set out above are agriculturally acceptable, the one chosen depending upon the particular use and upon the economics of the situation. Of particular utility are the alkali metal, alkaline earth, ammonium and amines salts.

The salts of the invention are frequently formed by reacting the precursors in aqueous solution. This solution can be evaporated to obtain the salt of the compound, usually as a dry powder. In some cases, it may be more convenient to use a non-aqueous solvent such as alcohols, acetones, etc. The resulting solution is then utilized in formulations which are treated to remove the solvent, for example, by evaporation under reduced pressure.

These pesticides which are suitable for use in the invention fulfill the above mentioned requirements for fire ant control and in addition, possess very little mammalian toxicity. They are also effective against other arthropods.

DETAILED DESCRIPTION OF THE INVENTION

Arthropod pests are suitably treated in accordance with the invention in any manner known to the prior art which is compatible with the above described toxicant compounds and mixtures. Suitable treatments include applying the toxicants as sprays in solutions, emulsions and dispersions; in traps with or without pheromone attractants and the like; and in bait formulations scattered in the vicinity of nests or in crop lands.

Substances suitable for use in this invention must be effective for at least one species of arthropod. However, there are several factors which may affect the effectiveness of specific substances with specific insects and with specific treatment techniques. These factors include:
1. Odor repellency.
2. Taste repellency.
3. Solubility in carriers such as solvents and baits.
4. Enzymatic effects.
5. Degradation by atmospheric oxygen, UV radiation and the like.

Using the invention for control of ants, in particular imported fire ants, it is preferable to prepare bait formulations into which the toxicants can be incorporated. The term "bait" is understood by those skilled in the art to be any substance that will entice the insect to ingest the toxicant. Suitable baits include edible oils and fats, vegetable seed meals, meat by-products such as blood, fish meal, syrups, honey, sucrose and other sugars, peanut butter, cereals and the like (see U.S. Pat. No. 3,220,921). Preferred baits for fire ants are mixtures of edible oils (as solvents for the toxicant compounds) with granular carriers such as corncob grits, pregel defatted corn grits and the like. These impregnated granular bait formulations readily fall to the ground when dispersed by arial or ground applicators where the ants forage, when found by the ants they are carried into the nest where the toxicants are ingested and distributed to workers and queen.

These compounds of the invention are known; but they are not known to be useful in pesticide formulations. Disclosures relevant to their preparation are found in the following U.S. patents:
2,803,615
2,346,612
2,732,378
2,759,019
2,803,656
2,915,554
3,398,182 and
3,787,351

The tests in the following examples indicate the effectiveness of the invention but are not intended to limit the invention's scope which is defined by the claims. All percentages and parts are by weight unless otherwise specified.

For fire ants any compound showing % mortality which is significantly greater than the bait without the toxicant is considered to be effective for the purposes of this invention. The use of preferred toxicants should result in less than 15% mortality at 24 hours and more than 50% and most preferably more than 85% mortality by the end of the test. The preferred compounds also should have at least a 10-fold difference between maximum and minimum dosages exhibiting delayed toxicity.

EXAMPLE 1

Each compound to be screened for fire ant toxicity was tested in 3 replications of 20 worker ants (*Solenopsis invicta*) which were placed in 30 ml cups for 14 days.

Cotton swabs saturated with soybean oil containing 1.0% of a test compound were offered to the ants in the cups for a 24 hour period. The swabs were removed and the ants remained without food for 24 hours. Cotton swabs saturated with SBO only were then placed in the cups and left there for the remainder of the testing period. Mortality counts were recorded for the test compounds and for a standard fire ant toxicant, Table 1.

EXAMPLE 2

Some of the compounds tested in Example 1 were retested as in Example 1 at concentrations of 0.01%, 0.10% and 1.0%, Table 2.

EXAMPLE 3

Some of the compounds listed in Table 1, which were not readily soluble in SBO were retested in the same manner as in Example 1 with the exception that SBO was replaced with a 1:1 v/v mixture of honey and water, Table 3.

EXAMPLE 4

Some of the preferred compounds from Example 2 were tested against duplicate laboratory colonies of fire ants.

The colonies consisted of a queen, eggs, larvae, pupae and greater than 40,000 workers. The test compounds were dissolved in SBO at 1.0% concentration and impregnated on pregel defatted corn grits so that the corn grits contained 30% SBO mixture. The test compound, therefore, was 0.30% of the total bait weight.

Five grams of the bait was made available to each colony for 4 days. The bait was removed and the colonies fed a standard diet for the remainder of the test which consisted of 1:1 honey-water mixture, boiled eggs and frozen fly pupae and cockroaches. Two colonies were treated with bait without toxicant as a control. Observation on the status of the queen and workers are recorded in Table 4. The ultimate fate of the colony is indicated as QD (queen dead) or CN (colony normal), Table 4.

EXAMPLE 5

Mixed sexes of adult house flies (*Musca domestica*) from an insecticide-resistant laboratory strain were fed after emergence exclusively on a fly food bait (6 parts sugar, 6 parts powdered nonfat dry milk, and 1 part powdered egg yolk) containing 1% of the test compounds. The bait was prepared by adding 10 ml of a solution or suspension of the test compound in a volatile solvent to 10 g of fly food in a small container. The solvent was allowed to evaporate for 4 to 6 hours, then the treated fly food was repulverized. The container of treated fly food and a container of water was placed in a cage with 100 newly emerged adult flies. Percent mortality for two replicate tests was determined after 3 days and compared to the results of feeding untreated fly food, Table 5.

Some of the above compounds may be more effective than the data indicates. If solubilities were poor in the SBO or honeywater formulation, concentrations of toxicants may not have reached the desired level. Many of these compounds showing poor effectiveness may be highly effective in other formulations.

EXAMPLE 6

Compounds 29757, 29758 and 29759 (see Table 1 for structures) were each dissolved in SBO at 1% concentration. Bait was prepared by impregnating the SBO mixture on pregel defatted corn grits so that the corn grit mixture contained 30% SBO mixture and 0.3% test compound. Compound 29759 was also used at 2.5% concentration so that it was 0.75% of the total bait weight.

Treated baits were scattered by tractor on field plots containing a number of active fire ant mounds at a concentration of one pound per acre. Other plots containing fire ant mounds were treated in the same manner with untreated pregel defatted corn grits and with grits treated with a standard fire ant toxicant as control. Results were evaluated as described by D. P. Harlan, W. H. Banks and C. E. Stringer, Southwest Entomologist, Vol. 6, pp 150-157, 1981, Table 6.

EXAMPLE 7

Compounds 29756, 29757, 29759 and 29778 were used to treat Orlando normal colonies of American cockroaches (*Periplaneta americana*) each containing 10 adults of mixed sexes as described by G. S. Burden, Pest Control Vol. 48, pp 22-24, 1980. A bait was formulated which consisted of a 3:1 mixture of cornmeal and powdered sugar containing 2.0% of the above compounds or a standard cockroach toxicant (trichlorfon). Untreated 3:1 mixture of cornmeal and powdered sugar was used as a control. A container with 2 grams of candidate or standard bait and a container with 2 grams of normal diet (Purina Lab Chow 5001) were placed in each arena with the cockroaches and left until the test was ended. Percent mortality is shown in Table 7.

EXAMPLE 8

Orlando normal colonies of German cockroaches (*Blattella germanica*) containing 25 adults were treated in the same manner as in Example 7. Results are shown in Table 8.

EXAMPLE 9

Twenty-five late 3rd- and early 4th-stage larvae of *Anopheles quadrimaculatus* were placed in a 500 ml glass jar (9×8.5 cm diam) containing 100 ml of well water, 0.05 g ground hog supplement for larval food, and a known amount of the candidate compound in not more than 1.0 ml acetone. The jars were covered with cloth netting and held in constant temperature incubators at 26.7°–28.9° C. (80°–84° F.) and 65–75% RH; a low level of illumination (ca. 0.5 footcandles inside the incubators) was maintained during nonworking hours. Seven days after set up, the jars were examined for the number of dead pupae, the number of adults that were dead or unable to complete eclosion, and the number of exuviae. The live adults were observed for gross abnormalities. Tests were replicated for at least 1 concn. and a standard larvicide, methoprene, was used as a control with each test series.

Several concns. of each compound were tested so that a dose-response relationship could be established. Using the Statistical Analysis System supported by NERDC, the resulting data were corrected for control mortality (Abbott's formula) and a probit analysis was made using log transformed mortality data. This analysis provided estimates for the LC-50 and LC-90, in ppm, for the compound.

EXAMPLE 10

Compounds were screened as mosquito larvicides (insect growth regulators, IGR) by exposing early 4th-instar larvae of *Anopheles quadrimaculatus* solutions or suspensions of the compounds in water (duplicate tests). The compounds were dissolved in acetone and added to water; water-soluble compounds remained in solution and the others became finely divided suspensions. Mosquito larvae were added to the treated water and mortality was determined after 24 hour of exposure. The compounds were initially tested at concns. of 10 and 1 parts per million. If 50% mortality occurred at 1 ppm, additional tests were conducted with lower concns. A standard larvicide, temephos (Abate), was tested as a control concurrently.

Results are shown in Table 10.

The following indicates the criteria for compounds tested against mosquitoes:

| Classification of IGR's Against Mosquitoes | | |
|---|---|---|
| Class | Criteria | LC-90 (ppm) |
| 1 | Ineffective at screening dose | >1.000 |
| 2 | Partially effective but not promising | 0.101–1.000 |
| 3 | Effective enough to justify full investigation | 0.021–0.100 |
| 4 | Exceptional | ≦0.020 |

Results are shown in Table 9.

TABLE I

| Number | Structure | Mortality at Specified Days % | | | | | | |
|---|---|---|---|---|---|---|---|---|
| | | 1 | 2 | 3 | 6 | 8 | 10 | 14 |
| 29752 | $C_2H_5$ $\phantom{xx}$ O<br>$\phantom{xxx}$ \|  $\phantom{xx}$ \|\|<br>$C_8F_{17}SO_2NC_2H_4OP(OH)_2$ | 2 | 3 | 3 | 3 | 3 | 3 | 10 |
| 29753 | $C_2H_5$<br>\|<br>$C_8F_{17}SO_2N(C_2H_4O)_3H$ | 0 | 0 | 0 | 8 | 65 | 87 | 93 |
| 29754 | $C_4H_9$<br>\|<br>$C_8F_{17}SO_2NC_2H_4OH$ | 0 | 0 | 0 | 3 | 32 | 72 | 93 |

TABLE I-continued

| Number | Structure | Mortality at Specified Days % | | | | | | |
|---|---|---|---|---|---|---|---|---|
| | | 1 | 2 | 3 | 6 | 8 | 10 | 14 |
| 29755 | $C_6F_{13}SO_2NC_2H_4OH$ with $C_2H_5$ on N | 0 | 0 | 0 | 17 | 38 | 87 | 97 |
| 29756 | $C_8F_{17}SO_2NC_4H_8OH$ with $CH_3$ on N | 3 | 3 | 13 | 73 | 90 | 97 | 98 |
| 29757 | $C_8F_{17}SO_2NC_2H_5$ with H on N | 33 | 88 | 100 | | | | |
| 29758 | $C_8F_{17}SO_2NCH_3$ with H on N | 18 | 88 | 100 | | | | |
| 29759 | $C_8F_{17}SO_2NH_2$ | 18 | 63 | 85 | 88 | 97 | 100 | |
| 29760 | $C_8F_{17}SO_3$—phenyl-$NH_2$ | 0 | 0 | 0 | 0 | 0 | 3 | 70 |
| 29761 | $C_8F_{17}SO_2NC_2H_4NH_2$ with H on N | 2 | 2 | 2 | 2 | 2 | 2 | 10 |
| 29762 | $C_8F_{17}SO_2N(C_2H_4NH)_2C_2H_4NH_2$ with $C_2H_5$ on N | 2 | 2 | 2 | 2 | 2 | 2 | 10 |
| 29763 | $C_6F_{13}SO_2N(C_2H_4O)_{12}H$ with $C_2H_5$ on N | 2 | 3 | 3 | 7 | 7 | 13 | 40 |
| 29764 | $C_{10}F_{21}SO_2N(C_2H_4O)_{14}H$ with $C_2H_5$ on N | 0 | 0 | 0 | 0 | 0 | 0 | 17 |
| 29765 | $C_8F_{17}SO_2N(C_2H_4OH)$ with $C_{12}H_{25}$ on N | 0 | 0 | 0 | 2 | 17 | 47 | 83 |
| 29766 | Adduct from 1 mole triphenylmethane triisocyanate, 1 mole $C_{18}H_{37}OH$ and 2 moles $C_8F_{17}SO_2NC_2H_4OH$ (with $C_2H_5$ on N) | 0 | 0 | 0 | 3 | 3 | 3 | 23 |
| 29767 | $C_8F_{17}SO_2NCH_2$-phenyl with $C_2H_5$ on N | 0 | 0 | 0 | 2 | 25 | 80 | 97 |
| 29768 | $C_8F_{17}SO_2N(C_2H_4O)_{12.5}CH_3$ with $C_2H_5$ on N | 0 | 0 | 0 | 7 | 42 | 87 | 97 |
| 29769 | $C_8F_{17}SO_2N(C_2H_4O)_{17}CH_3$ with $C_2H_5$ on N | 0 | 0 | 13 | 70 | 90 | 95 | 98 |
| 29770 | $C_6F_{13}SO_2NC_2H_5$ with H on N | 68 | 100 | | | | | |

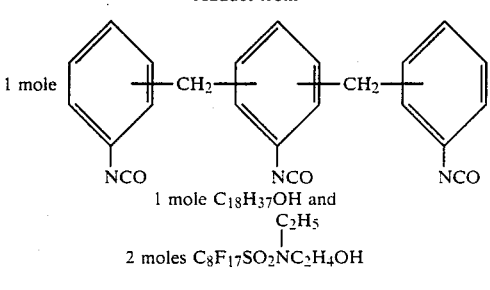

TABLE I-continued

| Number | Structure | Mortality at Specified Days % | | | | | | |
|---|---|---|---|---|---|---|---|---|
| | | 1 | 2 | 3 | 6 | 8 | 10 | 14 |
| 29771 | $C_8F_{17}SO_2NC_2H_4OCC_{17}H_{35}$ with $C_2H_5$ on N and $O\!=\!\!$ on C | 0 | 2 | 2 | 48 | 90 | 100 | |
| 29772 | $C_8F_{17}SO_2NC_2H_4O(C_3H_6O)_8H$ with $C_4H_9$ on N | 0 | 0 | 0 | 2 | 5 | 17 | 62 |
| 29773 | $C_8F_{17}SO_2NC_2H_4O(C_3H_6O)_8H$ with $C_2H_5$ on N | 0 | 2 | 2 | 2 | 2 | 12 | 43 |
| 29774 | $C_4F_9SO_2NC_{12}H_{25}$ with H on N | 0 | 0 | 0 | 0 | 2 | 3 | 7 |
| 29775 | $C_4F_9SO_2NC_3H_6N(CH_3)_2$ with $C_4H_9$ on N | 0 | 0 | 3 | 3 | 3 | 5 | 13 |
| 29776 | $C_8F_{17}SO_2NC_3H_6N(CH_3)_2$ with H on N | 0 | 0 | 0 | 0 | 0 | 3 | 23 |
| 29777 | $C_8F_{17}SO_2NC_{12}H_{25}$ with H on N | 0 | 0 | 5 | 47 | 82 | 98 | 100 |
| 29778 | $C_8F_{17}SO_2N$-pyrrole | 0 | 0 | 70 | 93 | 98 | 98 | 100 |
| 29779 | $C_2F_5C_6F_{10}SO_3K$ | 0 | 2 | 2 | 7 | 7 | 10 | 15 |
| 29780 | $C_7F_{15}CO_2NH_4$ | 0 | 0 | 2 | 2 | 3 | 3 | 5 |
| 29781 | $C_8F_{17}SO_2NCH_2$—C$_6H_4$—$SO_3Na$ with H on N | 0 | 0 | 0 | 18 | 40 | 80 | 97 |
| 29782 | $C_8F_{17}SO_2NC_2H_4OH$ with $C_2H_5$ on N | 0 | 0 | 5 | 15 | 53 | 83 | 100 |
| 50950 | $C_8F_{17}SO_3K$ | 0 | 0 | 0 | 0 | 0 | 0 | 0 |
| 10700 | $C_8F_{17}SO_2NNa$ with H on N | 0 | 3 | 7 | 58 | 70 | 80 | 87 |
| 10701 | $C_8F_{17}SO_2NNa$ with $CH_3$ on N | 0 | 15 | 80 | 97 | 98 | 98 | 100 |
| 10702 | $C_6F_{13}SO_2NH_2$ | 3 | 8 | 40 | 80 | 83 | 85 | 92 |
| 10703 | $CF_3SO_2NH_2$ | 3 | 13 | 25 | 58 | 70 | 72 | 72 |
| 10704 | $C_4F_9SO_2NCH_3$ with H on N | 68 | 97 | 100 | | | | |
| 10705 | $C_8F_{17}SO_2NCH_2CH$—$CH_2$ (epoxide) with $CH_3$ on N | 2 | 2 | 2 | 3 | 8 | 15 | 30 |
| 10706 | $C_8F_{17}SO_2N$—$C_2H_4CNH_2$ with $CH_3$ on N and $O\!=\!\!$ on C | 0 | 0 | 0 | 0 | 3 | 5 | 10 |
| 10707 | $C_8F_{17}SO_2N(C_2H_5)_2$ | 17 | 100 | | | | | |

TABLE I-continued

| Number | Structure | Mortality at Specified Days % | | | | | | |
|---|---|---|---|---|---|---|---|---|
| | | 1 | 2 | 3 | 6 | 8 | 10 | 14 |
| 10708 | $C_8F_{17}SO_2\underset{\underset{CH_3}{\|}}{N}(CH_2)_{10}\underset{\underset{CH_3}{\|}}{N}SO_2C_8F_{17}$ | 0 | 2 | 2 | 7 | 7 | 7 | 7 |
| 10709 | $C_8F_{17}SO_2\underset{\underset{C_2H_5}{\|}}{N}CH_2C{\equiv}CH$ | 0 | 2 | 2 | 48 | 53 | 72 | 85 |
| 10710 | $n\text{-}C_8F_{17}SO_2\underset{\underset{H}{\|}}{N}CH_2CH{=}CH_2$ | 2 | 25 | 55 | 90 | 95 | 98 | 98 |
| 10711 | $C_8F_{17}SO_2\underset{\underset{H}{\|}}{N}CH_2CH{=}CH_2$ | 0 | 12 | 40 | 93 | 97 | 98 | 98 |
| 10712 | $C_8F_{17}SO_2\underset{\underset{H}{\|}}{N}CH(CH_3)_2$ | 8 | 88 | 100 | | | | |
| 10713 | $C_8F_{17}SO_2\underset{\underset{H}{\|}}{N}C(CH_3)_3$ | 0 | 0 | 0 | 0 | 0 | 0 | 5 |
| 10714 | $C_8F_{17}SO_2\underset{\underset{H}{\|}}{N}C_6H_5$ (mixed isomers) | 75 | 82 | 82 | 90 | 90 | 92 | 93 |
| 10715 | $\underline{n}\text{-}C_8F_{17}SO_2\underset{\underset{H}{\|}}{N}C_6H_5$ (recrystalized linear isomers) | 68 | 82 | 85 | 92 | 92 | 92 | 100 |
| 10716 | $C_8F_{17}SO_2\underset{\underset{H}{\|}}{N}C_6H_5$ (branched isomers) | 52 | 63 | 63 | 77 | 83 | 88 | 90 |
| 10717 | $C_8F_{17}SO_2\underset{\underset{CH_3}{\|}}{N}CH{=}CH_2$ | 23 | 87 | 98 | 100 | | | |
| 10718 | $C_8F_{17}SO_2N\begin{cases}CH_2CH{=}CH_2\\CH_2\underset{\underset{OH}{\|}}{CH}CH_2Cl\end{cases}$ | 0 | 2 | 3 | 3 | 3 | 5 | 12 |
| 10719 | $[C_8H_{17}SO_2\underset{\underset{C_2H_5}{\|}}{N}C_2H_4O\overset{\overset{O}{\|}}{C}NH{-}\phantom{X}{-}CH_2{-}\phantom{X}{-}N{=}C{=}N{-}\phantom{X}]_2$ | 2 | 5 | 7 | 7 | 7 | 7 | 7 |
| 10720 | $[C_8F_{17}SO_2\underset{\underset{CH_3}{\|}}{N}C_2H_4O(CH_2\underset{\underset{CH_2Cl}{\|}}{CH}O)_5\overset{\overset{O}{\|}}{C}{-}\phantom{X}]_2$ | 0 | 0 | 0 | 3 | 7 | 12 | 32 |
| 10721 | $C_8H_{17}SO_2NH_2$ | 5 | 7 | 8 | 12 | 12 | 12 | 12 |
| 10722 | $C_8F_{17}SO_2\underset{\underset{H}{\|}}{N}C_{12}H_{25}$ | 0 | 0 | 0 | 2 | 3 | 3 | 3 |
| 10723 | $C_{17}H_{35}\overset{\overset{H}{\|}}{\underset{\underset{O}{\|}}{C}}N{-}\phantom{X}$ | 2 | 2 | 2 | 5 | 5 | 7 | 8 |

TABLE I-continued

| Number | Structure | Mortality at Specified Days % | | | | | | |
|---|---|---|---|---|---|---|---|---|
| | | 1 | 2 | 3 | 6 | 8 | 10 | 14 |
| 10724 | C$_8$F$_{17}$SO$_2$N(C$_2$H$_5$)CH$_2$CO$_2$H | 0 | 0 | 0 | 2 | 2 | 2 | 3 |
| 10725 | C$_8$F$_{17}$SO$_3$-C$_6$H$_3$(OH)-CO$_2$H | 0 | 0 | 0 | 0 | 7 | 18 | 52 |
| 10726 | C$_8$F$_{17}$SO$_3$-C$_6$H$_4$-NH-C(O)-C$_6$HCl$_3$-CO$_2$H | 0 | 0 | 0 | 0 | 0 | 0 | 0 |
| 10727 | C$_8$F$_{17}$SO$_3$H | 0 | 3 | 3 | 12 | 12 | 22 | 22 |
| 10728 | C$_6$F$_{13}$SO$_3$H | 0 | 0 | 0 | 3 | 7 | 7 | 8 |
| 10729 | C$_8$F$_{17}$SO$_2$N(C$_2$H$_5$)CH$_2$CO$_2$CH$_3$ | 0 | 0 | 0 | 7 | 13 | 25 | 50 |
| 10730 | C$_8$F$_{17}$SO$_2$N(C$_3$H$_7$)C$_2$H$_4$OH | 0 | 2 | 2 | 3 | 20 | 30 | 62 |
| 10731 | C$_8$F$_{17}$SO$_2$N(C$_2$H$_4$OH)$_2$ | 0 | 0 | 0 | 2 | 5 | 10 | 35 |
| 10732 | C$_8$F$_{17}$SO$_2$N(CH$_3$)CH$_2$CH(OH)—CH$_2$OH | 0 | 0 | 0 | 2 | 2 | 2 | 5 |
| 10733 | C$_8$F$_{17}$SO$_2$N(C$_2$H$_5$)C$_2$H$_4$Cl | 5 | 50 | 70 | 93 | 97 | 98 | 100 |
| 10734 | C$_8$F$_{17}$SO$_2$N(CH$_3$)C$_4$H$_8$SH | 2 | 3 | 5 | 5 | 8 | 20 | 57 |
| 10735 | C$_8$F$_{17}$C$_2$H$_4$SH | 3 | 3 | 3 | 3 | 3 | 5 | 5 |
| 10736 | [CF$_2$CF$_2$SO$_2$NH$_2$]$_2$ | 0 | 2 | 2 | 3 | 3 | 3 | 5 |
| 10737 | n-C$_3$F$_7$C(O)NH$_2$ | 0 | 3 | 3 | 10 | 10 | 10 | 25 |
| 10738 | C$_5$F$_{11}$C(O)NH$_2$ | 3 | 3 | 3 | 5 | 5 | 5 | 5 |
| 10739 | C$_7$F$_{15}$C(O)NH$_2$ | 0 | 0 | 0 | 2 | 2 | 2 | 2 |
| 10740 | C$_7$F$_{15}$C(O)N(H)CH$_2$C$_6$H$_5$ | 0 | 0 | 0 | 0 | 0 | 3 | 3 |
| 10741 | CF$_3$SO$_2$N(H)(CH$_3$) | 3 | 3 | 3 | 32 | 35 | 38 | 48 |
| 10742 | CF$_3$SO$_2$N(CH$_3$)$_2$ | 82 | 82 | 82 | 82 | 82 | 82 | 90 |

TABLE I-continued

| Number | Structure | Mortality at Specified Days % | | | | | | |
|---|---|---|---|---|---|---|---|---|
| | | 1 | 2 | 3 | 6 | 8 | 10 | 14 |
| 10743 | CF$_3$SO$_2$NH$_2$HN—(cyclohexyl)—O | 0 | 0 | 0 | 12 | 13 | 15 | 20 |
| 10744 | C$_2$F$_5$SO$_2$NH$_2$ | 3 | 17 | 22 | 35 | 40 | 45 | 50 |
| 10745 | C$_4$F$_9$SO$_2$NH$_2$ | 0 | 0 | 0 | 3 | 3 | 3 | 5 |
| 10746 | CF$_3$SO$_2$N(H)—C(=O)—C$_6$H$_5$ | 0 | 5 | 8 | 13 | 15 | 17 | 23 |
| 10747 | C$_4$F$_9$SO$_2$N(H)—C(=O)—C$_6$H$_5$ | 0 | 0 | 0 | 32 | 48 | 53 | 73 |
| 10748 | C$_8$F$_{17}$SO$_2$N(H)—C(=O)—C$_6$H$_5$ | 3 | 13 | 17 | 37 | 42 | 47 | 85 |
| 10749 | C$_8$F$_{17}$SO$_2$N(C$_2$H$_5$)—(C$_2$H$_4$O)$_7$CH$_3$ | 2 | 5 | 5 | 38 | 57 | 80 | 88 |
| 10750 | C$_8$F$_{17}$SO$_3^\ominus$ $^\oplus$N(C$_2$H$_5$)$_4$ | 0 | 0 | 0 | 3 | 3 | 3 | 7 |
| 10751 | C$_6$F$_{10}$(CH$_2$OH)$_2$ (Cyclic) | 2 | 5 | 5 | 23 | 28 | 32 | 58 |
| 10752 | FCH$_2$SO$_2$NH$_2$ | 0 | 0 | 2 | 30 | 33 | 43 | 53 |
| 10753 | HCF$_2$SO$_2$NH$_2$ | 0 | 2 | 2 | 13 | 18 | 20 | 30 |
| 10754 | CF$_3$CH$_2$SO$_2$NH$_2$ | 0 | 0 | 0 | 2 | 3 | 5 | 13 |
| | Standard | 0 | 12 | 97 | 100 | | | |
| | SBO | 0 | 0 | 0 | 5 | 8 | 9 | 13 |

TABLE 2

| Number | Structure | Conc. % | Percent Mortality at Specified Days | | | | | | | | |
|---|---|---|---|---|---|---|---|---|---|---|---|
| | | | 1 | 2 | 3 | 6 | 8 | 10 | 14 | 17 | 21 |
| 29753 | C$_8$F$_{17}$SO$_2$N(C$_2$H$_5$)(C$_2$H$_4$O)$_3$H | 0.01 | 0 | 0 | 0 | 0 | 3 | 7 | 7 | 13 | 20 |
| | | 0.1 | 0 | 0 | 0 | 0 | 0 | 0 | 3 | 7 | 27 |
| | | 1.0 | 0 | 0 | 2 | 52 | 87 | 98 | 99 | 100 | |
| 29754 | C$_8$F$_{17}$SO$_2$N(C$_4$H$_9$)C$_2$H$_4$OH | 0.01 | 0 | 0 | 0 | 0 | 0 | 0 | 0 | 0 | 2 |
| | | 0.1 | 0 | 2 | 2 | 3 | 3 | 3 | 25 | 48 | 78 |
| | | 1.0 | 0 | 0 | 0 | 0 | 0 | 40 | 92 | 98 | 100 |
| 29755 | C$_6$F$_{13}$SO$_2$N(C$_2$H$_5$)C$_2$H$_4$OH | 0.01 | 0 | 0 | 0 | 5 | 7 | 12 | 15 | 22 | 28 |
| | | 0.1 | 0 | 0 | 0 | 2 | 2 | 7 | 10 | 23 | 40 |
| | | 1.0 | 0 | 0 | 0 | 12 | 45 | 80 | 95 | 98 | 98 |
| 29756 | C$_8$F$_{17}$SO$_2$N(CH$_3$)C$_4$H$_8$OH | 0.01 | 0 | 0 | 2 | 5 | 8 | 8 | 8 | 10 | 13 |
| | | 0.1 | 0 | 0 | 0 | 2 | 5 | 30 | 75 | 85 | 92 |
| | | 1.0 | 0 | 2 | 10 | 83 | 85 | 95 | 100 | | |
| 29757 | C$_8$F$_{17}$SO$_2$N(H)C$_2$H$_5$ | 0.01 | 0 | 0 | 0 | 0 | 2 | 2 | 10 | 22 | 50 |
| | | 0.1 | 0 | 0 | 2 | 80 | 97 | 97 | 98 | 98 | 100 |
| | | 1.0 | 25 | 100 | | | | | | | |
| 29758 | C$_8$F$_{17}$SO$_2$N(H)CH$_3$ | 0.01 | 0 | 0 | 2 | 3 | 7 | 7 | 7 | 23 | 40 |
| | | 0.1 | 0 | 0 | 7 | 88 | 97 | 98 | 100 | | |
| | | 1.0 | 17 | 93 | 100 | | | | | | |
| 29759 | C$_8$F$_{17}$SO$_2$NH$_2$ | 0.01 | 0 | 0 | 0 | 3 | 7 | 7 | 10 | 20 | 23 |
| | | 0.1 | 0 | 0 | 0 | 2 | 33 | 77 | 92 | 95 | 98 |
| | | 1.0 | 43 | 85 | 98 | 100 | | | | | |
| 29765 | C$_8$F$_{17}$SO$_2$F$_{17}$SO$_2$N(C$_{12}$H$_{25}$)C$_2$H$_4$OH | 0.01 | 0 | 0 | 0 | 0 | 0 | 0 | 0 | 0 | 0 |
| | | 0.1 | 0 | 0 | 0 | 0 | 0 | 2 | 3 | 15 | |
| | | 1.0 | 0 | 0 | 0 | 0 | 2 | 32 | 77 | 88 | 100 |

TABLE 2-continued

| Number | Structure | Conc. % | \multicolumn{9}{c}{Percent Mortality at Specified Days} |
|---|---|---|---|---|---|---|---|---|---|---|---|
| | | | 1 | 2 | 3 | 6 | 8 | 10 | 14 | 17 | 21 |
| 29767 | $C_8F_{17}SO_2NCH_2$—phenyl, N-$C_2H_5$ | 0.01 | 0 | 0 | 0 | 0 | 0 | 3 | 3 | 3 | 3 |
| | | 0.1 | 0 | 0 | 0 | 2 | 2 | 3 | 8 | 18 | 42 |
| | | 1.0 | 0 | 0 | 0 | 2 | 42 | 83 | 100 | | |
| 29769 | $C_8F_{17}SO_2N(C_2H_4O)_{17}CH_3$, N-$C_2H_5$ | 0.01 | 0 | 0 | 0 | 3 | 7 | 7 | 10 | 13 | 17 |
| | | 0.1 | 0 | 0 | 0 | 2 | 3 | 5 | 10 | 25 | 48 |
| | | 1.0 | 0 | 0 | 32 | 100 | | | | | |
| 29770 | $C_6F_{13}SO_2NC_2H_5$, N-H | 0.01 | 2 | 2 | 3 | 5 | 7 | 8 | 10 | 13 | 15 |
| | | 0.1 | 0 | 2 | 2 | 5 | 7 | 17 | 48 | 58 | 70 |
| | | 1.0 | 47 | 98 | 98 | 100 | | | | | |
| 29771 | $C_8F_{17}SO_2NC_2H_4OCC_{17}H_{35}$, N-$C_2H_5$, O | 0.01 | 0 | 0 | 0 | 0 | 0 | 8 | 10 | 13 | 18 |
| | | 0.1 | 2 | 2 | 2 | 7 | 10 | 17 | 20 | 32 | 58 |
| | | 1.0 | 0 | 0 | 2 | 87 | 98 | 98 | 98 | 98 | 98 |
| 29772 | $C_8F_{17}SO_2NC_2H_4O(C_3H_6O)_8H$, N-$C_4H_9$ | 0.01 | 0 | 0 | 2 | 2 | 2 | 2 | 2 | 2 | 2 |
| | | 0.1 | 0 | 0 | 0 | 0 | 0 | 3 | 3 | 15 | 45 |
| | | 1.0 | 0 | 2 | 2 | 2 | 2 | 40 | 87 | 97 | 100 |
| 29773 | $C_8F_{17}SO_2NC_2H_4O(C_3H_6O)_8H$, N-$C_2H_5$ | 0.01 | 0 | 0 | 0 | 0 | 0 | 0 | 0 | 0 | 0 |
| | | 0.1 | 0 | 0 | 0 | 0 | 0 | 0 | 0 | 3 | 17 |
| | | 1.0 | 0 | 0 | 0 | 3 | 5 | 23 | 37 | 45 | 60 |
| 29776 | $C_8F_{17}SO_2NC_3H_6N(CH_3)_2$, N-H | 0.01 | 0 | 0 | 0 | 0 | 2 | 2 | 2 | 2 | 2 |
| | | 0.1 | 0 | 0 | 0 | 2 | 2 | 2 | 2 | 2 | 3 |
| | | 1.0 | 0 | 0 | 0 | 0 | 0 | 0 | 0 | 7 | 35 |
| 29777 | $C_8F_{17}SO_2NC_{12}H_{25}$, N-H | 0.01 | 0 | 0 | 0 | 5 | 5 | 5 | 7 | 13 | 17 |
| | | 0.1 | 0 | 0 | 0 | 0 | 2 | 2 | 20 | 50 | 80 |
| | | 1.0 | 0 | 2 | 3 | 78 | 97 | 100 | | | |
| 29778 | $C_8F_{17}SO_2N$ (pyrrole) | 0.01 | 2 | 3 | 3 | 8 | 8 | 8 | 13 | 15 | 18 |
| | | 0.1 | 0 | 2 | 3 | 10 | 10 | 52 | 67 | 80 | 88 |
| | | 1.0 | 0 | 2 | 17 | 92 | 100 | | | | |
| 29779 | $C_2F_5C_6F_{10}SO_3K$ | 0.01 | 0 | 0 | 0 | 2 | 2 | 2 | 2 | 2 | 2 |
| | | 0.1 | 0 | 0 | 0 | 0 | 2 | 3 | 3 | 3 | 3 |
| | | 1.0 | 0 | 0 | 0 | 0 | 2 | 2 | 5 | 5 | 7 |
| 29781 | $C_8F_{17}SO_2NCH_2$—phenyl—$SO_3Na$, N-H | 0.01 | 0 | 0 | 0 | 2 | 2 | 5 | 5 | 7 | 7 |
| | | 0.1 | 0 | 0 | 0 | 3 | 3 | 5 | 8 | 12 | 23 |
| | | 1.0 | 0 | 0 | 0 | 77 | 93 | 95 | 100 | | |
| 29782 | $C_8F_{17}SO_2NC_2H_4OH$, N-$C_2H_5$ | 0.01 | 0 | 0 | 2 | 2 | 2 | 2 | 2 | 2 | 3 |
| | | 0.1 | 0 | 0 | 0 | 0 | 2 | 2 | 8 | 40 | 60 |
| | | 1.0 | 0 | 0 | 0 | 45 | 67 | 88 | 98 | 100 | |
| 10700 | $C_8F_{17}SO_2NNa$, N-H | 0.01 | 2 | 3 | 3 | 7 | 7 | 7 | 8 | 12 | 15 |
| | | 0.1 | 2 | 3 | 3 | 8 | 12 | 40 | 70 | 82 | 95 |
| | | 1.0 | 0 | 2 | 10 | 75 | 88 | 93 | 98 | 100 | |
| 10701 | $C_8F_{17}SO_2NNa$, N-$CH_3$ | 0.01 | 0 | 0 | 0 | 0 | 0 | 0 | 0 | 2 | 7 |
| | | 0.1 | 0 | 0 | 0 | 18 | 65 | 83 | 95 | 97 | 98 |
| | | 1.0 | 23 | 87 | 100 | | | | | | |
| 10702 | $C_6F_{13}SO_2NH_2$ | 0.01 | 0 | 0 | 0 | 2 | 2 | 2 | 2 | 5 | 12 |
| | | 0.1 | 3 | 7 | 7 | 7 | 7 | 17 | 63 | 77 | 92 |
| | | 1.0 | 0 | 3 | 30 | 67 | 75 | 87 | 95 | 98 | 100 |
| 10703 | $CF_3SO_2NH_2$ | 0.01 | 0 | 0 | 0 | 3 | 3 | 5 | 7 | 8 | 17 |
| | | 0.1 | 3 | 3 | 3 | 5 | 5 | 5 | 17 | 27 | 58 |
| | | 1.0 | 2 | 8 | 18 | 33 | 42 | 50 | 67 | 73 | 82 |
| 10704 | $C_4F_9SO_2NCH_3$, N-H | 0.01 | 0 | 2 | 3 | 7 | 7 | 8 | 8 | 15 | 27 |
| | | 0.1 | 2 | 2 | 2 | 3 | 3 | 3 | 3 | 3 | 10 |
| | | 1.0 | 87 | 98 | 98 | 98 | 98 | 100 | | | |
| 10707 | $C_8F_{17}SO_2N(C_2H_5)_2$ | 0.01 | 0 | 0 | 0 | 2 | 5 | 10 | 20 | 50 | 60 |
| | | 0.1 | 0 | 7 | 13 | 78 | 92 | 98 | 100 | | |
| | | 1.0 | 30 | 100 | | | | | | | |

TABLE 2-continued

| Number | Structure | Conc. % | \multicolumn{9}{c}{Percent Mortality at Specified Days} |
| --- | --- | --- | --- | --- | --- | --- | --- | --- | --- | --- | --- |
| | | | 1 | 2 | 3 | 6 | 8 | 10 | 14 | 17 | 21 |
| 10709 | $C_8F_{17}SO_2NCH_2C\equiv CH$ with $C_2H_5$ | 0.01 | 5 | 5 | 5 | 5 | 5 | 5 | 15 | 15 | 30 |
| | | 0.1 | 2 | 2 | 2 | 2 | 3 | 5 | 43 | 73 | 87 |
| | | 1.0 | 0 | 0 | 0 | 2 | 45 | 60 | 90 | 93 | 100 |
| 10710 | $\underline{n}\text{-}C_8F_{17}SO_2NCH_2CH=CH_2$ with H | 0.01 | 2 | 2 | 2 | 2 | 2 | 2 | 12 | 37 | 75 |
| | | 0.1 | 3 | 3 | 3 | 48 | 60 | 78 | 93 | 98 | 100 |
| | | 1.0 | 13 | 53 | 80 | 100 | | | | | |
| 10711 | $C_8F_{17}SO_2NCH_2CH=CH_2$ with H | 0.01 | 2 | 2 | 2 | 3 | 5 | 5 | 5 | 7 | 28 |
| | | 0.1 | 3 | 3 | 3 | 18 | 42 | 85 | 97 | 98 | 100 |
| | | 1.0 | 23 | 57 | 72 | 88 | 100 | | | | |
| 10712 | $C_8F_{17}SO_2NCH(CH_3)_2$ with H | 0.01 | 2 | 2 | 2 | 2 | 2 | 3 | 5 | 27 | 65 |
| | | 0.1 | 0 | 0 | 10 | 75 | 93 | 98 | 100 | | |
| | | 1.0 | 83 | 97 | 100 | | | | | | |
| 10714 | $C_8F_{17}SO_2NC_6H_5$ with H (mixed isomers) | 0.01 | 0 | 0 | 0 | 2 | 3 | 3 | 7 | 17 | 27 |
| | | 0.1 | 0 | 2 | 2 | 8 | 53 | 70 | 93 | 95 | 98 |
| | | 1.0 | 83 | 87 | 88 | 95 | 97 | 97 | 100 | | |
| 10715 | $\underline{n}\text{-}C_8F_{17}SO_2NC_6H_5$ with H (recrystallized linear isomer) | 0.01 | 2 | 2 | 2 | 2 | 2 | 2 | 3 | 12 | 27 |
| | | 0.1 | 0 | 0 | 0 | 18 | 63 | 87 | 90 | 95 | 98 |
| | | 1.0 | 88 | 92 | 93 | 97 | 98 | 98 | 98 | 98 | 100 |
| 10716 | $C_8F_{17}SO_2NC_6H_5$ with H (branched isomer) | 0.01 | 2 | 5 | 5 | 8 | 8 | 8 | 8 | 13 | 27 |
| | | 0.1 | 0 | 3 | 3 | 12 | 40 | 70 | 93 | 97 | 97 |
| | | 1.0 | 78 | 83 | 87 | 100 | | | | | |
| 10717 | $C_8F_{17}SO_2NCH=CH_2$ with $CH_3$ | 0.01 | 0 | 0 | 0 | 8 | 8 | 13 | 25 | 37 | 57 |
| | | 0.1 | 0 | 7 | 33 | 77 | 90 | 92 | 100 | | |
| | | 1.0 | 100 | | | | | | | | |
| 10733 | $C_8F_{17}SO_2NC_2H_4Cl$ with $C_2H_5$ | 0.01 | 0 | 0 | 0 | 0 | 3 | 3 | 5 | 23 | 47 |
| | | 0.1 | 0 | 0 | 2 | 22 | 83 | 95 | 97 | 100 | |
| | | 1.0 | 57 | 87 | 98 | 100 | | | | | |
| 10742 | $CF_3SO_2N(CH_3)_2$ | 0.01 | 0 | 0 | 0 | 0 | 0 | 3 | 12 | 13 | 30 |
| | | 0.1 | 0 | 0 | 3 | 3 | 5 | 8 | 17 | 35 | 53 |
| | | 1.0 | 88 | 90 | 90 | 97 | 98 | 98 | 98 | 98 | 100 |
| 10749 | $C_8F_{17}SO_2N(C_2H_4O)_7CH_3$ with $C_2H_5$ | 0.01 | 2 | 3 | 3 | 3 | 3 | 5 | 8 | | |
| | | 0.1 | 5 | 5 | 8 | 15 | 20 | 23 | 40 | | |
| | | 1.0 | 2 | 5 | 5 | 38 | 57 | 80 | 88 | | |
| — | Copolymer of 30% $C_8F_{17}SO_2NC_2H_4$— with $C_4H_9$ <br> $OC(O)-C(=CH_2)$ <br> 70% $CH_2=CHCO(C_2H_4O)_{10}$— <br> $(C_3H_6O)_{22}(C_2H_4O)_{10}$— <br> $OCCH=CH_2$ | 0.01 | — | — | — | — | — | — | — | — | — |
| | | 0.1 | 0 | 8 | 10 | 18 | 18 | 20 | 52 | — | 87 |
| | | 1.0 | 3 | 3 | 7 | 13 | 15 | 22 | 47 | — | 73 |
| — | 50% Copolymer of 30% $C_8F_{17}SO_2NC_2H_4$— with $C_2H_5$ <br> $OC(O)-C(CH_3)=CH_2$ <br> 70% $CH_3O(C_2H_4O)_{16}$ <br> $C(O)-C(H)=CH_2$ | 0.01 | — | — | — | — | — | — | — | — | — |
| | | 0.1 | 2 | 3 | 5 | 10 | 12 | 13 | 30 | — | 80 |
| | | 1.0 | 5 | 7 | 7 | 15 | 22 | 25 | 58 | — | 78 |

TABLE 2-continued

| Number | Structure | Conc. % | Percent Mortality at Specified Days | | | | | | | | |
|---|---|---|---|---|---|---|---|---|---|---|---|
| | | | 1 | 2 | 3 | 6 | 8 | 10 | 14 | 17 | 21 |
| | 50% $C_2H_5O\overset{O}{\overset{\|}{C}}CH_3$ | | | | | | | | | | |
| Standard | | 0.01 | 0 | 0 | 0 | 0 | 12 | 37 | 48 | 62 | 83 |
| | | 0.1 | 3 | 5 | 20 | 88 | 97 | 100 | | | |
| | | 1.0 | 2 | 75 | 100 | | | | | | |
| SBO | | | 0 | 1 | 1 | 3 | 6 | 11 | 13 | 19 | 22 |

TABLE 3

| Numbers | Structure | Conc. % | PERCENT MORTALITY AT SPECIFIED DAYS | | | | | | |
|---|---|---|---|---|---|---|---|---|---|
| | | | 1 | 2 | 3 | 6 | 8 | 10 | 14 |
| 50950 | $C_8F_{17}SO_3K$ | 1.0 | 2 | 2 | 23 | 87 | 100 | | |
| 10700 | $C_8F_{17}SO_2\overset{H}{\overset{\|}{N}}Na$ | 1.0 | 2 | 37 | 73 | 98 | 100 | | |
| 10701 | $C_8F_{17}SO_2\overset{CH_3}{\overset{\|}{N}}Na$ | 1.0 | 62 | 97 | 100 | | | | |
| 10705 | $C_8F_{17}SO_2\overset{CH_3}{\overset{\|}{N}}CH_2CH\overset{O}{\overset{\diagup\diagdown}{\phantom{x}}}CH_2$ | 1.0 | 0 | 0 | 0 | 0 | 0 | 8 | 42 |
| 10706 | $C_8F_{17}SO_2\overset{CH_3}{\overset{\|}{N}}C_2H_4\overset{O}{\overset{\|}{C}}NH_2$ | 1.0 | 0 | 0 | 2 | 2 | 2 | 7 | 62 |
| 10708 | $C_8F_{17}SO_2\overset{CH_3}{\overset{\|}{N}}(CH_2)_{10}\overset{CH_3}{\overset{\|}{N}}SO_2C_8F_{17}$ | 1.0 | 0 | 0 | 0 | 0 | 0 | 0 | 35 |
| 10710 | $\underline{n}\text{-}C_8F_{17}SO_2\overset{H}{\overset{\|}{N}}CH_2CH=CH_2$ | 1.0 | 0 | 12 | 55 | 97 | 97 | 98 | 100 |
| 10712 | $C_8F_{17}SO_2\overset{H}{\overset{\|}{N}}CH(CH_3)_2$ | 1.0 | 23 | 100 | | | | | |
| 10719 | $[C_8F_{17}SO_2\overset{C_2H_5}{\overset{\|}{N}}C_2H_4O\overset{O}{\overset{\|}{C}}NH-\underset{\phantom{x}}{\bigcirc}-CH_2-\underset{\phantom{x}}{\bigcirc}-N=C=N-\underset{\phantom{x}}{\bigcirc}]_{\overline{n}}$ | 1.0 | 0 | 0 | 3 | 10 | 33 | 55 | 85 |
| 10720 | $[C_8F_{17}SO_2\overset{CH_3}{\overset{\|}{N}}C_2H_4O-(CH_2CHO)_5\overset{O}{\overset{\|}{C}}\underset{CH_2Cl}{\underset{\|}{\phantom{x}}}-\underset{\phantom{x}}{\bigcirc}]_{\overline{n}}$ | 1.0 | 10 | 22 | 33 | 33 | 33 | 35 | 43 |
| 10722 | $C_8H_{17}SO_2\overset{H}{\overset{\|}{N}}C_{12}H_{25}$ | 1.0 | 0 | 0 | 0 | 0 | 2 | 3 | 5 |
| 10723 | $C_{17}H_{35}\overset{O}{\overset{\|}{C}}\overset{H}{\overset{\|}{N}}-\underset{\phantom{x}}{\bigcirc}$ | 1.0 | 0 | 0 | 0 | 0 | 0 | 0 | 0 |

TABLE 3-continued

| Numbers | Structure | Conc. % | \multicolumn{7}{c}{PERCENT MORTALITY AT SPECIFIED DAYS} |
| --- | --- | --- | --- | --- | --- | --- | --- | --- | --- |
| | | | 1 | 2 | 3 | 6 | 8 | 10 | 14 |
| 10724 | $C_8F_{17}SO_2NCH_2CO_2H$ with $C_2H_5$ on N | 1.0 | 0 | 0 | 2 | 7 | 7 | 10 | 12 |
| 10725 | $C_8F_{17}SO_3$—C$_6$H$_3$(OH)(CO$_2$H) (salicylate derivative) | 1.0 | 0 | 0 | 2 | 2 | 3 | 5 | 8 |
| 10726 | $C_8F_{17}SO_3$—C$_6$H$_4$—NHC(O)— (tetrachlorobenzoic acid amide) | 1.0 | 0 | 0 | 0 | 0 | 0 | 2 | 5 |
| 10727 | $C_8F_{17}SO_3H$ | 1.0 | 0 | 37 | 62 | 95 | 100 | | |
| 10728 | $C_6F_{13}SO_3H$ | 1.0 | 15 | 77 | 95 | 100 | | | |
| 10729 | $C_8F_{17}SO_2NCH_2CO_2CH_3$ with $C_2H_5$ on N | 1.0 | 0 | 0 | 0 | 22 | 40 | 58 | 90 |
| 10730 | $C_8F_{17}SO_2NC_2H_4OH$ with $C_3H_7$ on N | 1.0 | 0 | 0 | 0 | 0 | 2 | 12 | 77 |
| 10731 | $C_8F_{17}SO_2N(C_2H_4OH)_2$ | 1.0 | 0 | 0 | 0 | 0 | 0 | 25 | 57 |
| 10732 | $C_8F_{17}SO_2NCH_2CH$—$CH_2$ with $CH_3$ on N, OH OH | 1.0 | 0 | 0 | 0 | 0 | 0 | 0 | 2 |
| 10734 | $C_8F_{17}SO_2NC_4H_8SH$ with $CH_3$ on N | 1.0 | 0 | 0 | 0 | 2 | 2 | 2 | 5 |
| 10738 | $C_5F_{11}C(O)NH_2$ | 1.0 | 0 | 0 | 2 | 2 | 2 | 7 | 10 |
| 10739 | $C_7F_{15}C(O)NH_2$ | 1.0 | 0 | 0 | 0 | 2 | 3 | 17 | 35 |
| 10740 | $C_7F_{15}C(OH)=NCH_2C_6H_5$ | 1.0 | 0 | 0 | 0 | 0 | 2 | 2 | 2 |
| 10743 | $CF_3SO_2NH_2 \cdot HN$(morpholine) | 1.0 | 0 | 2 | 2 | 15 | 27 | 42 | 57 |
| 10748 | $C_8F_{17}SO_2N(H)$—C(O)—C$_6$H$_5$ | 1.0 | 0 | 0 | 0 | 2 | 3 | 13 | 63 |
| 10750 | $C_8F_{17}SO_3^{\ominus} \ ^{\oplus}N(C_2H_5)_4$ | 1.0 | 10 | 47 | 95 | 100 | | | |
| 10752 | $FCH_2SO_2NH_2$ | 1.0 | 0 | 0 | 0 | 2 | 5 | 17 | 45 |
| 10754 | $CF_3CH_2SO_2NH_2$ | 1.0 | 0 | 0 | 0 | 0 | 0 | 2 | 18 |
| — | Copolymer of | 1.0 | 0 | 7 | 12 | 20 | 20 | 25 | 52 | 62 |

TABLE 3-continued

| Numbers | Structure | Conc. % | \multicolumn{7}{c}{PERCENT MORTALITY AT SPECIFIED DAYS} |
|---------|-----------|---------|---|---|---|---|---|---|---|
| | | | 1 | 2 | 3 | 6 | 8 | 10 | 14 |
| | 30% $C_8F_{17}SO_2NC_2H_4-$ with $C_4H_9$ substituent, $OC(=O)-C(H)=CH_2$ | | | | | | | | | |
| | 70% $CH_2=CHCO(C_2H_4O)_{10}-(C_3H_6O)_{22}(C_2H_4O)_{10}-$ $C(=O)-C(H)=CH_2$ | | | | | | | | | |
| — | 50% of Copolymer 30% $C_8F_{17}SO_2NC_2H_4-$ with $C_2H_5$ substituent, $OC(=O)-C(CH_3)=CH_2$ 70% $CH_3O(C_2H_4O)_{16}C(=O)-C(H)=CH_2$ 50% $C_2H_4OC(=O)CH_3$ | 1.0 | 0 | 2 | 2 | 10 | 13 | 18 | 40 | 73 |
| Standard | | 1.0 | 0 | 100 | | | | | |
| Honey:Water | | | 0 | 0 | 0 | 0 | 0 | 1 | 1 |

TABLE 4

| Number | Structure | \multicolumn{6}{c}{Percent worker mortality after following days of initial exposure to bait} |
|--------|-----------|---|---|---|---|---|---|
| | | 2 | 10 | 14 | 16 | 23 | 26 |
| 29757 | H (i.e., $C_8F_{17}SO_2NH-$) | 40 | 87 | 95 QD | | | |
| 29757 | $C_8F_{17}SO_2NC_2H_5$ (H) | 10 | 50 | 75 | 92 QD | | |
| 29758 | H | 10 | 30 | 50 | 75 | 90 | 92 QD |
| 29758 | $C_8F_{17}SO_2NCH_3$ (H) | 5 | 28 | 35 QD | | | |
| 29759 | $C_8F_{17}SO_2NH_2$ | 15 | 50 | 65 QD | | | |
| 29759 | | 8 | 25 | 30 | 30 | 50 QD | |
| 29778 | $C_8F_{17}SO_2N$(pyrrole) | 0 | 10 | 35 | 50 QD | | |
| 29778 | | 0 | 15 QD | | | | |
| Control | | 0 | 1 | 2 | 2 | 2 | 2 CN |
| Control | | 0 | 2 | 3 | 3 | 5 | 5 CN |

TABLE 5

| Number | Structure | % Mortality After 3 Days |
|--------|-----------|--------------------------|
| 29756 | $C_8F_{17}SO_2NC_4H_8OH$ with $CH_3$ substituent | 0 |
| 29757 | $C_8F_{17}SO_2NC_2H_5$ with H substituent | 0 |
| 29758 | $C_8F_{17}SO_2NCH_3$ with H substituent | 0 |
| 29759 | $C_8F_{17}SO_2NH_2$ | 80 |
| 29778 | $C_8F_{17}SO_2N$(pyrrole) | 60 |
| Untreated Fly Food | | 0 |

TABLE 6

| Treatment | Conc. % | \multicolumn{3}{c}{Population Index} |
|-----------|---------|---|---|---|
| | | Pre-treatment | 6 weeks | % Reduction |
| Untreated | | 305 | 305 | 0 |
| | | 130 | 155 | 0 |
| | | 105 | 185 | 0 |
| Standard | 1 | 120 | 19 | 84 |

TABLE 6-continued

| Treatment | Conc. % | Population Index Pre-treatment | 6 weeks | % Reduction |
|---|---|---|---|---|
|  |  | 140 | 0 | 100 |
|  |  | 255 | 15 | 94 |
| 29758 | 1 | 170 | 0 | 100 |
|  |  | 190 | 7 | 96 |
|  |  | 170 | 0 | 100 |
| 29757 | 1 | 150 | 0 | 100 |
|  |  | 160 | 48 | 70 |
|  |  | 160 | 32 | 80 |
| 29759 | 2.5 | 195 | 2 | 99 |
|  |  | 180 | 0 | 100 |
|  |  | 175 | 25 | 86 |
| 29759 | 1 | 165 | 0 | 100 |
|  |  | 195 | 25 | 87 |
|  |  | 180 | 81 | 55 |

TABLE 7

| Treatment | Percent Mortality After Indicated Days | | | | |
|---|---|---|---|---|---|
|  | 1 | 2 | 3 | 7 | 10 |
| 29756 | 0 | 0 | 0 | 60 | 100 |
|  | 0 | 0 | 20 | 100 |  |
| 29757 | 0 | 10 | 30 | 90 | 100 |
|  | 0 | 40 | 40 | 100 |  |
| 29758 | 0 | 30 | 40 | 80 | 100 |
|  | 0 | 20 | 30 | 90 | 100 |
| 29759 | 20 | 50 | 90 | 100 |  |
|  | 30 | 80 | 90 | 100 |  |
| 29778 | 0 | 20 | 40 | 100 |  |
|  | 0 | 50 | 80 | 100 |  |
| Standard | 100 |  |  |  |  |
|  | 100 |  |  |  |  |
| Cornmeal-Powdered | 0 | 0 | 0 | 0 | 0 |
| Sugar Mixture | 0 | 0 | 0 | 0 | 0 |

TABLE 8

| Treatment | Percent Mortality After Indicated Days | | | | |
|---|---|---|---|---|---|
|  | 1 | 2 | 3 | 7 | 10 |
| 29756 | 44 | 88 | 100 |  |  |
|  | 56 | 100 |  |  |  |
|  | 68 | 88 | 96 | 100 |  |
|  | 68 | 88 | 100 |  |  |
| 29757 | 88 | 100 |  |  |  |
|  | 92 | 96 | 100 |  |  |
|  | 92 | 92 | 100 |  |  |
|  | 88 | 96 | 96 | 100 |  |
| 29758 | 84 | 84 | 92 | 100 |  |
|  | 80 | 92 | 100 |  |  |
|  | 76 | 88 | 96 | 100 |  |
|  | 88 | 92 | 96 | 100 |  |
| 29759 | 84 | 92 | 100 |  |  |
|  | 96 | 96 | 100 |  |  |
|  | 100 |  |  |  |  |
|  | 96 | 100 |  |  |  |
| 29778 | 100 |  |  |  |  |
|  | 92 | 96 | 100 |  |  |
|  | 96 | 96 | 100 |  |  |
|  | 96 | 100 |  |  |  |
| Standard | 100 |  |  |  |  |
|  | 92 | 96 | 96 | 100 |  |
|  | 100 |  |  |  |  |
|  | 100 |  |  |  |  |
| Cornmeal-powdered | 0 | 0 | 0 | 0 | 0 |
| Sugar Mixture | 0 | 0 | 0 | 0 | 0 |
|  | 0 | 0 | 0 | 0 | 0 |
|  | 0 | 0 | 0 | 0 | 0 |

TABLE 9

| Chemical Code No. | Lethal Concentration (ppm) | |
|---|---|---|
|  | LC-50 | LC-90 |
| 29756 | 0.0167 | 0.0486 |

TABLE 9-continued

| Chemical Code No. | Lethal Concentration (ppm) | |
|---|---|---|
|  | LC-50 | LC-90 |
| 29757 | .0054 | .0200 |
| 29758 | .0067 | .0274 |
| 29759 | .0029 | .0081 |
| 29778 | .0209 | .0374 |
| Control | .0016 | .0069 |

TABLE 10

| Chemical Code No. | % Mortality After 24 hrs., Conc. (ppm) | | | | |
|---|---|---|---|---|---|
|  | 10 | 1.0 | 0.1 | 0.01 | 0.001 |
| 29756 | 100 | 96 | 0 |  |  |
| 29757 | 100 | 96 | 34 |  |  |
| 29758 | 100 | 82 | 78 |  |  |
| 29759 | 100 | 16 | 0 |  |  |
| 29778 | 44 | 22 | 0 |  |  |
| Control |  |  |  | 98 | 38 |

We claim:

1. A method for the control of a population of arthropods comprising the step of treating said arthropods with an effective amount of a toxicant substance or mixture of substances having the structural formula:

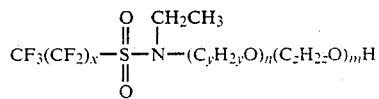

wherein x=4 to 19, y=1 to 4, z=1 to 4 and n+m=1 to 20.

2. A method for the control of a population of arthropods comprising the step of treating said arthropods with an effective amount of a toxicant substance or mixture of substances having the structural formula:

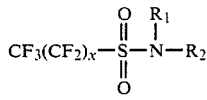

wherein x=4 to 19 and $R_1$ and $R_2$ are selected from the group consisting of H and alkyl groups containing 1 to 12 carbon atoms.

3. A method for the control of a population of arthropods comprising the step of treating said arthropods with an effective amount of a toxicant substance having the structural formula:

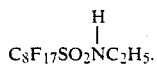

4. The method of claim 3, wherein said arthropods are selected from the group consisting of ants, cockroaches, flies, mosquitoes and termites.

5. A method for the control of a population of arthropods comprising the step of treating said arthropods with an effective amount of a toxicant substance or mixture of substances having the structural formula:

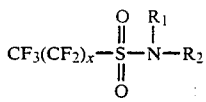

wherein x=4 to 19; $R_2$ is selected from the group consisting of sodium, potassium, calcium, lithium, barium, magnesium, zinc, iron, and aluminum; and $R_1$ is selected from the group consisting of H, alkyl, alkenyl, $CH_2C\equiv CH$, phenyl, aralkyl, $O=C-C_6H_5$, hydroxyalkyl, $CH_2CO_2H$, carboxyalkyl esters and a group of the structure $-(C_yH_{2y}O)_nR_3$ wherein n=1 to 20, y=1 to 4 and $R_3$ is selected from the same group as $R_1$.

6. The method of claim 5, wherein $R_2$ is sodium.
7. The method of claim 5, wherein $R_2$ is potassium.
8. The method of claim 5, wherein said $R_1$ is alkyl.
9. The method of claim 5, wherein said $R_1$ is alkenyl.
10. The method of claim 5, wherein said $R_1$ is $CH_2C\equiv CH$.
11. The method of claim 5, wherein said $R_1$ is phenyl.
12. The method of claim 5, wherein said $R_1$ is aralkyl.
13. The method of claim 5, wherein said $R_1$ is $O=C-C_6H_5$.
14. The method of claim 5, wherein said $R_1$ is hydroxyalkyl.
15. The method of claim 5, wherein said $R_1$ is $CH_2CO_2H$.
16. The method of claim 5, wherein said $R_1$ is carboxyalkyl esters.
17. The method of claim 5, wherein said $R_1$ is a group of the structure $-(C_yH_{2y}O)_nR_3$ wherein n=1 to 20, y=1 to 4 and $R_3$ is selected from the same group as $R_1$.
18. The method of claim 5, wherein said arthropods are selected from the group consisting of ants, cockroaches, flies, mosquitoes and termites.
19. A method for the control of a population of arthropods comprising the step of treating said arthropods with an effective amount of a toxicant substance or mixture of substances having the structural formula:

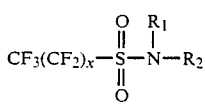

wherein x=4 to 19; $R_1$ and $R_2$ are selected from the group consisting of H, alkyl, alkenyl, $CH_2C\equiv CH$, phenyl, aralkyl, $O=C-C_6H_5$, hydroxyalkyl, $CH_2CO_2H$, carboxyalkyl esters, and a group of the structure $-(C_zH_{2z}O)_nR_3$ wherein n=1 to 20, z=1 to 4 and $R_3$ is selected from the same group as $R_1$ and $R_2$.

20. The method of claim 19, wherein said $R_1$ or $R_2$ is alkyl.
21. The method of claim 19, wherein said $R_1$ or $R_2$ is alkenyl.
22. The method of claim 19, wherein said $R_1$ or $R_2$ is $CH_2C\equiv CH$.
23. The method of claim 19, wherein said $R_1$ or $R_2$ is phenyl.
24. The method of claim 19, wherein said $R_1$ or $R_2$ is aralkyl.
25. The method of claim 19, wherein said $R_1$ or $R_2$ is $O=C-C_6H_5$.
26. The method of claim 19, wherein said $R_1$ or $R_2$ is hydroxyalkyl.
27. The method of claim 19, wherein said $R_1$ or $R_2$ is $CH_2CO_2H$.
28. The method of claim 19, wherein said $R_1$ or $R_2$ is carboxyalkyl esters.
29. The method of claim 19, wherein said $R_1$ or $R_2$ is a group of the structure $-(C_yH_{2y}O)_nR_3$ wherein n=1 to 20, y=1 to 4 and $R_3$ is selected from the same group as $R_1$.
30. The method of claim 19, wherein said arthropods are selected from the group consisting of ants, cockroaches, flies, mosquitoes and termites.
31. A method for the control of a population of arthropods comprising the step of treating said arthropods with an effective amount of a toxicant substance or mixture of substances having the structural formula:

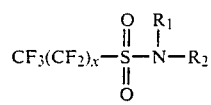

wherein x=4 to 19; $R_2$ is ammonium; and $R_1$ is selected from the group consisting of H, alkyl, alkenyl, $CH_2C\equiv CH$, phenyl, aralkyl, $O=C-C_6H_5$, hydroxyalkyl, $CH_2CO_2H$, carboxyalkyl esters and a group of the structure $-(C_yH_{2y}O)_nR_3$ wherein n=1 to 20, y=1 to 4 and $R_3$ is selected from the same group as $R_1$.

32. The method of claim 31, wherein said arthropods are selected from the group consisting of ants, cockroaches, flies, mosquitoes and termites.
33. A composition for the control of a population of arthropods, said composition comprising:
(1) An effective amount of a toxicant substance having the structural formula:

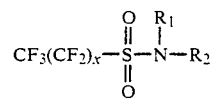

wherein x=4 to 19; $R_2$ is ammonium; and $R_1$ is selected from the group consisting of H, alkyl, alkenyl, $CH_2C\equiv CH$, phenyl, aralkyl, $O=C-C_6H_5$, hydroxyalkyl, $CH_2CO_2H$, carboxyalkyl esters and a group of the structure $-(C_yH_{2y}O)_nR_3$ wherein n=1 to 20, y=1 to 4 and $R_3$ is selected from the same group as $R_1$; and
(2) A bait component for arthropods.

34. A composition for the control of a population of arthropods, said composition comprising:
(1) An effective amount of a toxicant substance having the structural formula:

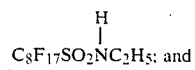

(2) A bait component for arthropods.

35. The component of claim 34 further comprising a carrier for said toxicant substance and said bait.
36. A composition for the control of a population of arthropods, said composition comprising:
(1) An effective amount of a toxicant substance having the structural formula:

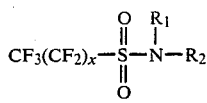

wherein x=4 to 19; $R_1$ and $R_2$ are selected from the group consisting of H, alkyl, alkenyl, $CH_2C\equiv CH$, phenyl, aralkyl, $O=C\text{-}C_6H_5$, hydroxyalkyl, $CH_2CO_2H$, carboxyalkyl esters, and a group of the structure $-(C_zH_{2z}O)_nR_3$ wherein n=1 to 20, z=1 to 4 and $R_3$ is selected from the same group as $R_1$ and $R_2$; and (2) A bait component for arthropods.

37. A composition for the control of a population of arthropods, said composition comprising:

(1) An effective amount of a toxicant substance having the structural formula:

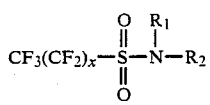

wherein x=4 to 19; $R_2$ is selected from the group consisting of sodium, potassium, calcium, lithium, barium, magnesium, zinc, iron, and aluminum; and $R_1$ is selected from the group consisting of H, alkyl, alkenyl, $CH_2C\equiv CH$, phenyl, aralkyl, $O=C\text{-}C_6H_5$, hydroxyalkyl, $CH_2CO_2H$, carboxyalkyl esters and a group of the structure $-(C_yH_{2y}O)_nR_3$ wherein n=1 to 20, y=1 to 4 and $R_3$ is selected from the same group as $R_1$; and (2) A bait component for arthropods.

38. The composition of claim 37, wherein said $R_2$ is sodium.

39. The composition of claim 37, wherein said $R_2$ is potassium.

40. The composition of claim 37, wherein said $R_1$ is alkyl.

41. The composition of claim 37, wherein said $R_1$ is alkenyl.

42. The composition of claim 37, wherein said $R_1$ is $CH_2C\equiv CH$.

43. The composition of claim 37, wherein said $R_1$ is phenyl.

44. The composition of claim 37, wherein said $R_1$ is aralkyl.

45. The composition of claim 37, wherein said $R_1$ is $O=C\text{-}C_6H_5$.

46. The composition of claim 37, wherein said $R_1$ is hydroxyalkyl.

47. The composition of claim 37, wherein said $R_1$ is $CH_2CO_2H$.

48. The composition of claim 37, wherein said $R_1$ is carboxyalkyl esters.

49. The composition of claim 37, wherein said $R_1$ is a group of the structure $-(C_yH_{2y}O)_nR_3$ wherein n=1 to 20, y=1 to 4 and $R_3$ is selected from the same group as $R_1$.

* * * * *

UNITED STATES PATENT AND TRADEMARK OFFICE
CERTIFICATE OF CORRECTION

PATENT NO. : 4,921,696
DATED : May 1, 1990
INVENTOR(S) : Vander Meer et al.

It is certified that error appears in the above-identified patent and that said Letters Patent is hereby corrected as shown below:

On the title page, section [75], add co-inventors --William E. Meyers of San Ramon, CA; Danny H. Lewis of Hartselle, AL.-- following "all of Gainsville, Fla."; in Section [75] third line, replace "Gainsville" with --Gainesville--; and in section [63] fourth line, replace "Apr. 16, 1984" with --Apr. 10, 1984--. In column 1, line 19, replace "damaging" with --damage--; and line 58, replace "salts" with --salt--. In column 2, line 10, replace "porton" with --portion--; line 24, replace "$(C_yH_{2y}O)mR_3$" with --$(C_yH_{2y}O)_mR_3$--; line 34, replace "compund" with --compound--; and line 61, replace "amines" with --amine--. In column 3, line 44, replace "arial" with --aerial--; and lines 44-45, replace "forage, when" with --forage. When--. In column 4, line 11, insert --(SBO)--following "soybean oil". In column 6, line 32, replace "hour" with --hours--. In Table 1, the formula for compound 29765 should appear as follows:

$$\underset{C_8F_{17}SO_2NC_2H_4OH}{\overset{C_{12}H_{25}}{|}}$$

; the formula for compound 29775 should appear as follows:

$$\underset{C_4F_9SO_2NC_3H_6N(CH_3)_2}{\overset{H}{|}}$$

; and the formula for 10726 should appear as follows: 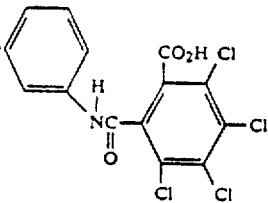

In Table 2, the formula for compound 29765 should appear as follows:

$$\underset{C_8F_{17}SO_2NC_2H_4OH}{\overset{C_{12}H_{25}}{|}}$$

; and the formula for compound 29767 should appear as follows: 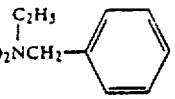

UNITED STATES PATENT AND TRADEMARK OFFICE
CERTIFICATE OF CORRECTION

PATENT NO. : 4,921,696

DATED : May 1, 1990

INVENTOR(S) : Vander Meer et al.

It is certified that error appears in the above-identified patent and that said Letters Patent is hereby corrected as shown below:

In Table 3, the formula for compound 10723 should appear as follows: 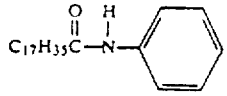 ; and the formula for compound 10743 should appear as follows: $CF_3SO_2NH_2 \cdot HN\text{—}\bigcirc\text{—}O$ Signed and Sealed this Seventeenth Day of September, 1991

Attest:

HARRY F. MANBECK, JR.

*Attesting Officer*     *Commissioner of Patents and Trademarks*